(12) United States Patent
Zhang et al.

(10) Patent No.: US 8,986,535 B2
(45) Date of Patent: Mar. 24, 2015

(54) ERYTHROPOIETIN RECEPTOR MODIFIED ELECTRODE AND ITS PREPARATION METHOD AND APPLICATION

(71) Applicant: First Affiliated Hospital, Third Military Medical University, Chinese People's Liberation Army, Chongqing (CN)

(72) Inventors: Liqun Zhang, Chongqing (CN); Yunxia Wang, Chongqing (CN); Weiling Fu, Chongqing (CN)

(73) Assignee: First Affiliated Hospital, Third Military Medical University, Chinese People's Liberation Army, Chongqing (CN)

( * ) Notice: Subject to any disclaimer, the term of this patent is extended or adjusted under 35 U.S.C. 154(b) by 0 days.

(21) Appl. No.: 14/007,350

(22) PCT Filed: Oct. 9, 2012

(86) PCT No.: PCT/CN2012/082621
§ 371 (c)(1),
(2) Date: Sep. 25, 2013

(87) PCT Pub. No.: WO2014/036772
PCT Pub. Date: Mar. 13, 2014

(65) Prior Publication Data
US 2014/0216950 A1 Aug. 7, 2014

(30) Foreign Application Priority Data
Sep. 7, 2012 (CN) .......................... 2012 1 0328850

(51) Int. Cl.
*G01N 27/327* (2006.01)
*G01N 33/487* (2006.01)
*B05D 3/00* (2006.01)
*G01N 33/74* (2006.01)

(52) U.S. Cl.
CPC ........ *G01N 27/3275* (2013.01); *G01N 27/3276* (2013.01); *G01N 33/48714* (2013.01); *B05D 3/002* (2013.01); *G01N 33/746* (2013.01); *G01N 27/3277* (2013.01)
USPC .................. 205/792; 204/403.01; 427/126.2; 435/7.1; 435/287.1; 422/68.1; 422/82.01

(58) Field of Classification Search
CPC .......... G01N 27/3275; G01N 27/3276; G01N 27/327; G01N 27/3277; G01N 33/746; G01N 33/487; B05D 3/002

USPC ......... 204/775, 777.5, 780.5, 403.14, 403.01; 435/287.1, 7.1; 422/68.1, 82.01; 205/792

See application file for complete search history.

(56) References Cited

U.S. PATENT DOCUMENTS

| | | | |
|---|---|---|---|
| 2005/0095698 A1 * | 5/2005 | Carlson | ...................... 435/287.2 |
| 2009/0008247 A1 | 1/2009 | Chen et al. | |
| 2010/0101965 A1 * | 4/2010 | Sasaki et al. | .................. 205/775 |

FOREIGN PATENT DOCUMENTS

| | | |
|---|---|---|
| CN | 1472529 | 2/2004 |
| CN | 101625334 | 1/2010 |
| CN | 101672814 | 3/2010 |
| WO | 99/22227 | 5/1999 |
| WO | 02/088732 | 11/2002 |

OTHER PUBLICATIONS

Liu et al. (Electroanalysis 2005, 17, No. 12).*
Zhang et al. (Biosensors andBioelectronics50(2013)217-223).*
Lei et al. (Colloids and Surfaces B: Biointerfaces 82 (2011) 168-172).*

* cited by examiner

*Primary Examiner* — Jennifer Dieterle
(74) *Attorney, Agent, or Firm* — Hamre, Schumann, Mueller & Larson, P.C.

(57) ABSTRACT

The invention discloses an erythropoietin receptor modified electrode, which is a glassy carbon electrode with erythropoietin receptor as recognition element fixed onto the electrode surface via ZnO sol-gel. The modified electrode can be prepared easily, and its performance is stable. After 50-day storage in the dark at 4° C., its response current remained approximately 77% of the original value. An electrochemical biosensor using this modified electrode as working electrode, a platinum electrode as counter electrode, a saturated calomel electrode as reference electrode, and 2 mmol/L $K_3[Fe(CN)_6]$—$K_4[Fe(CN)_6]$phosphate buffer as the test base solution, can detect erythropoietin (EPO) and/or recombinant human erythropoietin (rhEPO) in a fast, specific, and sensitive manner, with a linear range of 5 pg/L-500 ng/L and a limit of detection of 0.5 pg/L. In particular, according to peak potential differences, the biosensor allows accurate discrimination of EPO and rhEPO. It may be used not only for detection of low concentrations of EPO or rhEPO, but also for detection of the stimulant rhEPO in sports games.

10 Claims, 5 Drawing Sheets

Dilution ratio of ZnO sol-gel stock solution and absolute alcohol

Vol/vol ratio of ZnO sol-gel stock solution and EPOR solution

ERYTHROPOIETIN RECEPTOR MODIFIED ELECTRODE AND ITS PREPARATION METHOD AND APPLICATION

FIELD OF THE INVENTION

The invention belongs to the technical field of electrochemical detection. It concerns a modified electrode and its preparation method, and also concerns an electrochemical biosensor comprising the modified electrode as working electrode and its detection method.

BACKGROUND

Erythropoietin (EPO) is a glycoprotein hormone and hematopoietic factor, which is mainly produced in the human kidney. EPO promotes the production and release of red cells in bone marrow. In 1985, recombinant human erythropoietin (rhEPO) was synthesized by gene engineering. Due to its mitogenic and differentiation-promoting actions, rhEPO can bring about the effect of blood transfusion, while not putting patients on risk of viral infection or excessive transfusion. Hence, it has played an important role in treating renal anemia. Meanwhile, rhEPO is a novel stimulant in sports games due to its action of increasing oxygen carrying capacity and exercise tolerance. In 2005, rhEPO was listed by the International Olympic Committee (IOC) and World Anti-Doping Agency (WADA) as the first peptide substance banned in sports games.

EPO and rhEPO have the same biologic activities and very similar molecular structure, and their only difference lies in the isoelectric point. EPO has an isoelectric point of 3.7-4.7, and rhEPO has an isoelectric point of 4.4-5.1. Therefore, it is difficult to discriminate EPO from rhEPO. EPO and rhEPO discrimination has long been relying on the combination of mass spectrometry, isoelectric focusing and gel electrophoresis. Nevertheless, these detection methods have some drawbacks, such as long separation time, low detection efficiency, and poor specificity. Therefore, they are not fit for fast, accurate discrimination of EPO and rhEPO. It is imperative to develop a highly specific, sensitive, fast, and accurate method to discriminate EPO and rhEPO.

SUMMARY

One problem to be solved by the herein disclosed invention is to provide a modified electrode. A further problem to be solved is to provide a said modified electrode preparation method. A still further problem to be solved is to provide an electrochemical biosensor utilizing the modified electrode as working electrode. A still further problem to be solved is to provide an EPO and/or rhEPO detection method using the said electrochemical biosensor. The said modified electrode can be prepared easily, and its performance is stable. The electrochemical biosensor using the modified electrode as working electrode is able to detect EPO and/or rhEPO in a fast, specific, sensitive manner. In particular, it allows fast, accurate discrimination of EPO and rhEPO.

The problems are solved by providing the following technical protocols:

1. Erythropoietin receptor (EPOR) modified electrode. The said modified electrode is a glassy carbon electrode with EPOR as recognition element fixed onto the electrode surface via ZnO sol-gel.

2. EPOR modified electrode preparation method, including the following steps:
    a. Glassy carbon electrode pretreatment: The glassy carbon electrode surface is burnished, cleaned, and dried for later use;
    b. ZnO sol-gel preparation: Zinc acetate is dissolved in absolute alcohol. While the mixture is subjected to ultrasound stirring, lithium hydroxide is added to obtain ZnO sol-gel solution for later use;
    c. EPOR fixation: ZnO sol-gel solution prepared at step b and EPOR solution mixed thoroughly, and the resulting solution is dripped onto the surface of glassy carbon electrode pretreated as described in step a, followed by drying and washes. Now the erythropoietin receptor modified electrode is prepared.

Preferably, at the said step a, glassy carbon electrode is burnished first with 0.3 µm, and then with 0.05 µm aluminum oxide powder. Between burnishes, the electrode is washed first with water, and then in an ultrasound bath with nitric acid, acetone and water. After each wash, the electrode is air dried.

Preferably, at the said step b, zinc acetate is dissolved in absolute alcohol to obtain 0.1 mol/L solution. While the mixture is subjected to ultrasound stirring, lithium hydroxide is added to obtain ZnO sol-gel stock solution with a final concentration of 0.067 mol/L. Immediately prior to use, ZnO sol-gel solution is prepared by diluting the stock solution with absolute alcohol at vol/vol ratios of 2:1~1:3.

More preferably, at the said step b, zinc acetate is dissolved in absolute alcohol to obtain 0.1 mol/L solution. While the mixture is subjected to ultrasound stirring, lithium hydroxide is added to obtain ZnO sol-gel stock solution with a final concentration of 0.067 mol/L. Immediately prior to use, ZnO sol-gel solution is prepared by diluting the stock solution with absolute alcohol at a vol/vol ratio of 1:2.

Preferably, at the said step c, ZnO sol-gel solution prepared at step b and 10 ng/L~100 m/L erythropoietin receptor solution are mixed thoroughly at vol/vol ratios of 4:1~1:1.15, and the resulting solution is dripped onto the surface of glassy carbon electrode pretreated as described in step a, followed by air drying and thorough washes in phosphate buffer. Now erythropoietin receptor modified electrode is prepared.

More preferably, at the said step c, ZnO sol-gel solution prepared at step b and 1 µg/L erythropoietin receptor solution are mixed thoroughly at a vol/vol ratio of 1:1, and the resulting solution is dripped onto the surface of glassy carbon electrode pretreated as described in step a, followed by air drying and thorough washes in phosphate buffer. Now the erythropoietin receptor modified electrode is prepared.

3. EPO and rhEPO electrochemical biosensor comprises a working electrode, a counter electrode, a reference electrode and the test base solution. The said working electrode is the erythropoietin receptor modified electrode said by claim 1, the counter electrode is platinum electrode, and the reference electrode is saturated calomel electrode. The said test base solution is phosphate buffer (pH=6.2~9.0) containing 2 mmol/L $K_3[Fe(CN)_6]$ and 2 mmol/L $K_4[Fe(CN)_6]$.

Preferably, the said test base solution is phosphate buffer (pH=7.4) containing 2 mmol/L $K_3[Fe(CN)_6]$ and 2 mmol/L $K_4[Fe(CN)_6]$.

4. EPO and/or rhEPO is detected using the said EPO and rhEPO electrochemical biosensor as follow: the erythropoietin receptor modified electrode and sample solution are co-incubated for over 20 minutes, then cyclic voltammetric scanning is performed using the electrochemical biosensor comprising the erythropoietin receptor modified electrode as working electrode, a platinum electrode as counter electrode, a saturated calomel electrode as reference electrode, and phosphate buffer (pH=6.2~9.0) containing 2 mmol/L $K_3[Fe(CN)_6]$ and 2 mmol/L $K_4[Fe(CN)_6]$ as the test base solution, with the potential scanning range of –0.3V~0.7V, and with the potential scanning speed of 10 mv/s~100 mv/s. The sample solution's erythropoietin concentration is calculated according to the peak current at the potential of 0.14V~0.17 V and the erythropoietin standard curve, and/or the sample solution's concentration of recombinant human erythropoietin is calculated according to the peak current at the potential of 0.06V~0.09 V and the recombinant human erythropoietin standard curve.

Preferably, the said EPOR modified electrode and sample solution are co-incubated for 20 minutes, and the said potential scanning speed is 50 mv/s.

The benefits of the invention lie in: The invented EPOR modified electrode can be prepared easily, and its performance is stable. After 50-day storage in the dark at 4° C., its response current remained approximately 77% of the original value. An electrochemical biosensor using this modified electrode as working electrode can detect erythropoietin (EPO) and/or recombinant human erythropoietin (rhEPO) in a fast, specific, and sensitive manner, with a linear range of 5 pg/L-500 ng/L and a limit of detection of 0.5 pg/L. In particular, according to peak potential differences, the biosensor allows accurate discrimination of EPO and rhEPO. It may be used not only for detection of low concentrations of EPO or rhEPO, but also for detection of the stimulant rhEPO in sports games.

DETAILED DESCRIPTION

In order to make clear the objectives, technical protocol and advantages of the invention, the preferred embodiments of the invention are described in detail below with reference to the drawings.

The reagents and instruments used in the embodiments are listed below: lithium hydroxide (LiOH•$H_2O$), zinc acetate [$Zn(Ac)_2$•$2H_2O$] from Shanghai Sangon Bioengineering Co., Ltd (Shanghai, China); $K_3[Fe(CN)_6]$, $K_4[Fe(CN)_6]$ from Chongqing Dongfang Reagents Factory (Chongqing, China); glassy carbon electrode, saturated calomel electrode, platinum electrode, 0.3 μm and 0.05 μm $Al_2O_3$ powder from Tianjin Aidahengsheng Tech Co., Ltd (Tianjin, China); PBS powder from Beijing Zhong Shan Golden Bridge Biotech Co., Ltd (Beijing, China); EPOR from Novus Biologicals (USA); EPO and rhEPO standard preparations from Abnova (USA); Model CHI660C electrochemical workstation from Shanghai Chenhua Instruments Co., Ltd, China; model KQ-5200B ultrasound washer from Kunshan Ultrasound Instruments Co., Ltd (Jiangsu, China), and model ZD-2 automatic electric potential titrimeter from Shanghai Jingke Leici Co., Ltd (Shanghai, China).

I. EPOR Modified Electrode Preparation and Parameter Optimization

The preparation method of EPOR modified electrode includes the following steps:

a. Glassy carbon electrode pretreatment: Glassy carbon electrodes (3 mm in diameter) are burnished first with 0.3 μm, and then with 0.05 μm $Al_2O_3$ powder. Between burnishes, the electrodes are washed first with ultrapure water, and then in an ultrasound bath with nitric acid, acetone and ultrapure water each for 5 min. After wash, the electrodes are air dried.

b. ZnO sol-gel solution preparation: 2.20 g (0.01 mol) of $Zn(Ac)_2$•$2H_2O$ is dissolved in 100 mL of absolute alcohol. Then, 0.28 g (6.7 mmol) LiOH•$H_2O$ is added slowly under sonication to prepare ZnO sol-gel stock solution, which is stored at 4° C. for later use. Immediately prior to use, ZnO sol-gel solution is prepared by diluting the stock solution with absolute alcohol at a vol/vol ratio of 1:2.

c. EPOR fixation: ZnO sol-gel solution prepared at step b and 1 μg/L EPOR solution are mixed thoroughly at the vol/vol ratio of 1:1, and 10 μl of the resulting solution is dripped onto the surface of glassy carbon electrode pretreated as described in step a, followed by drying at room temperature for 16 hours allowing formation of gel on the electrode surface. Finally, the electrode is washed thoroughly in PBS solution (pH 7.4, 0.05 mol/L). The prepared EPOR modified electrode is stored at 4° C. in dark prior to use.

Figure 1:
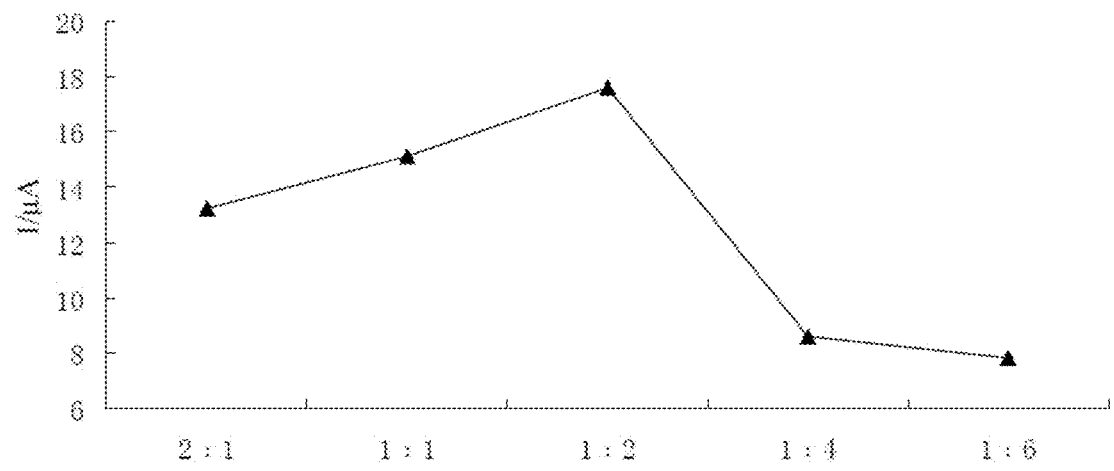
FIG. 1 shows the effect of the dilution ratio of ZnO sol-gel stock solution and absolute alcohol on the current response of EPOR modified electrode.
Figure 2:
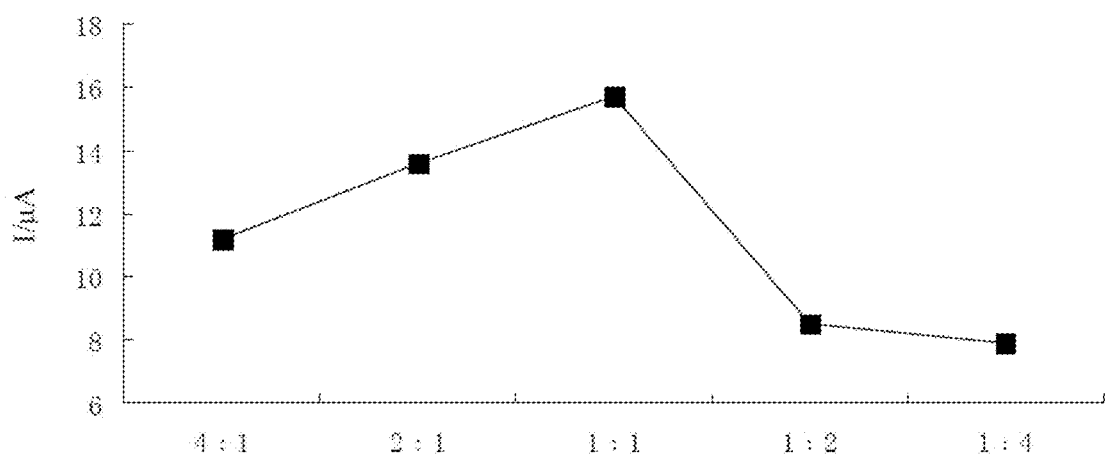
FIG. 2 shows the effect of the vol/vol ratio of ZnO sol-gel solution and EPOR solution on the current response of EPOR modified electrode.
Figure 3:
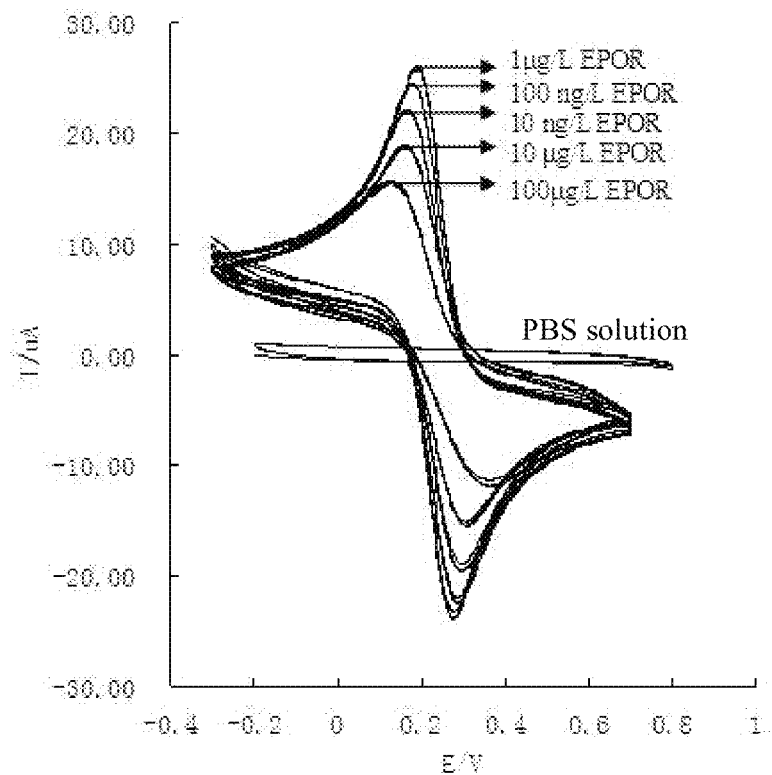
FIG. 3 shows the effect of EPOR solution concentration on the current response of EPOR modified electrode.

The invention involves optimization of major parameters that influence the current response of EPOR modified electrodes. Electrochemical biosensor comprising EPOR modified electrode prepared with various parameters as working electrode, saturated calomel electrode as reference electrode, platinum electrode as counter electrode, and PBS solution containing 2 mmol/L $K_3[Fe(CN)_6]$—$K_4[Fe(CN)_6]$ (pH 7.4, 0.05 mol/L) as the test base solution is used for cyclic voltammetric scanning at room temperature, within the potential scanning range of −0.3V~0.7V, and with the potential scanning speed of 50 mv/s. The results show that the dilution ratio of ZnO sol-gel stock solution and absolute alcohol, the vol/vol ratio of ZnO sol-gel solution and EPOR solution, and EPOR concentration affect the current response of EPOR modified electrode, and that the preferred dilution ratio ranges 2:1~1:3 and the most preferred ratio is 1:2 for ZnO sol-gel stock solution and absolute alcohol (FIG. 1). The preferred vol/vol ratio of ZnO sol-gel solution and EPOR solution ranges 4:1~1:1.15, and the most preferred ratio is 1:1 (FIG. 2). The preferred EPOR concentration ranges 10 ng/L~100 µg/L, and the most preferred concentration is 1 µg/L (FIG. 3).

II. Fabrication of Electrochemical Biosensor for EPO and rhEPO and Parameter Optimization EPOR modified electrode and the sample solution are co-incubated for 20 minutes, and EPO and rhEPO electrochemical biosensor comprising EPOR modified electrode as working electrode, saturated calomel electrode as reference electrode, platinum electrode as counter electrode fabrication, and PBS solution containing 2 mmol/L $K_3[Fe(CN)_6]$—$K_4[Fe(CN)_6]$ (pH 7.4, 0.05 mol/L) as the test base solution is used for cyclic voltammetric scanning at room temperature, within the potential scanning range of −0.3V~0.7V, and with the potential scanning speed of 50 mv/s.

Figure 4:
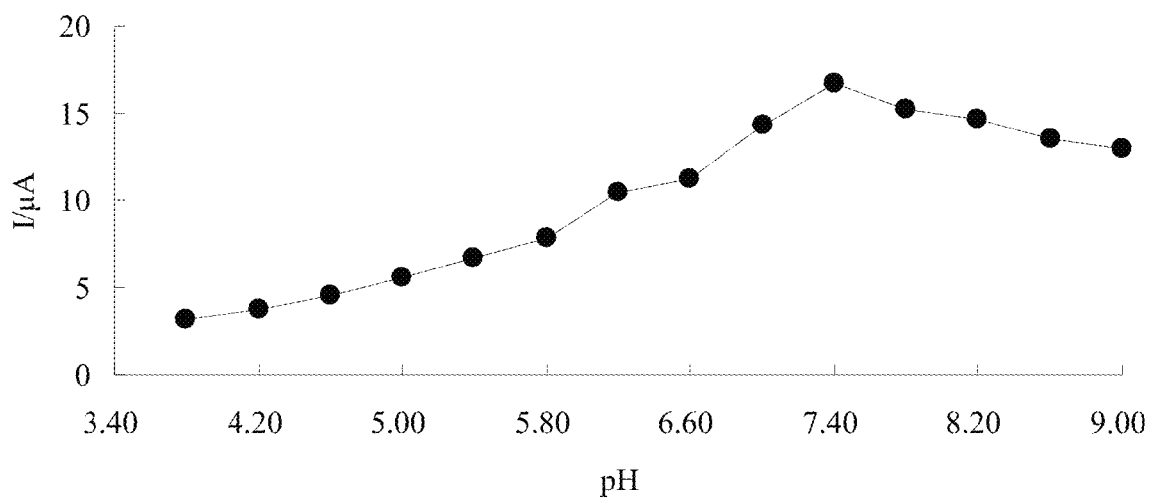
FIG. 4 shows the effect of pH value of test base solution on the current response of EPO and rhEPO electrochemical biosensor.
Figure 5:
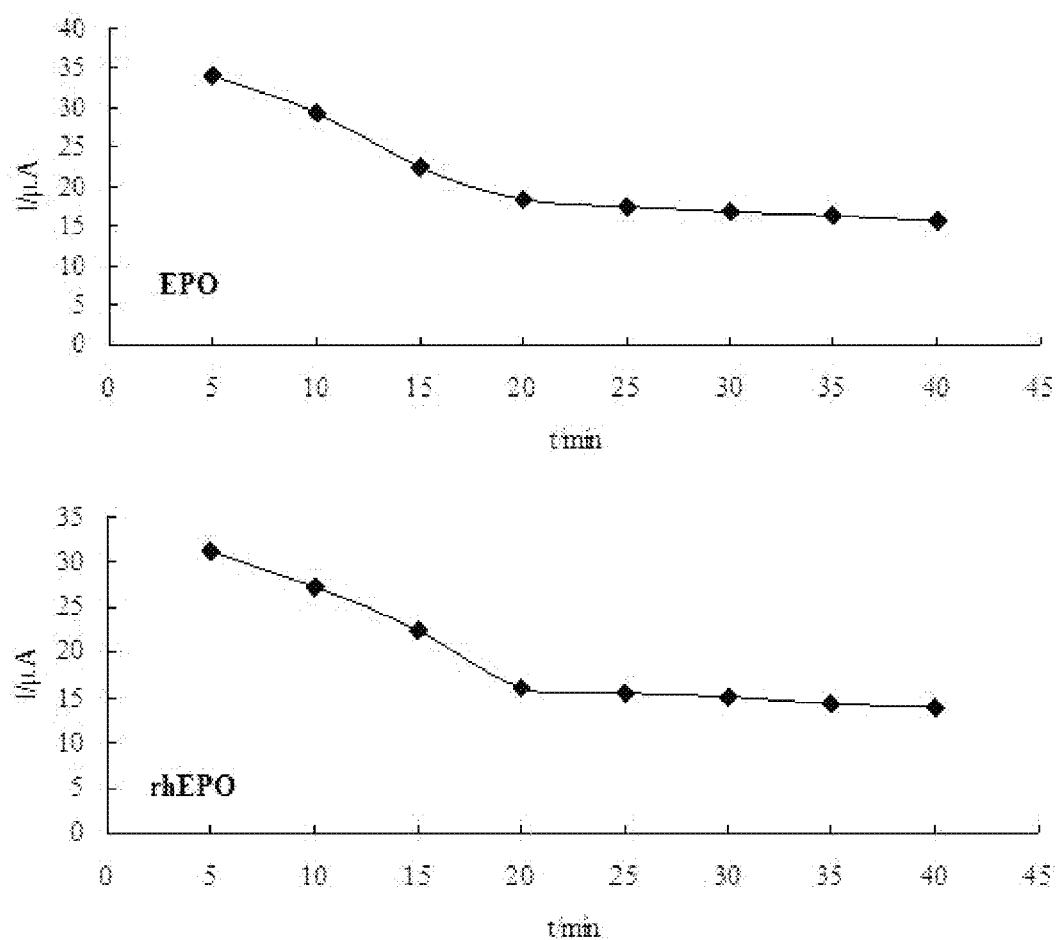
FIG. 5 shows the effect of working electrode incubation time in the sample solution on the current response of EPO and rhEPO electrochemical biosensor.
Figure 6:
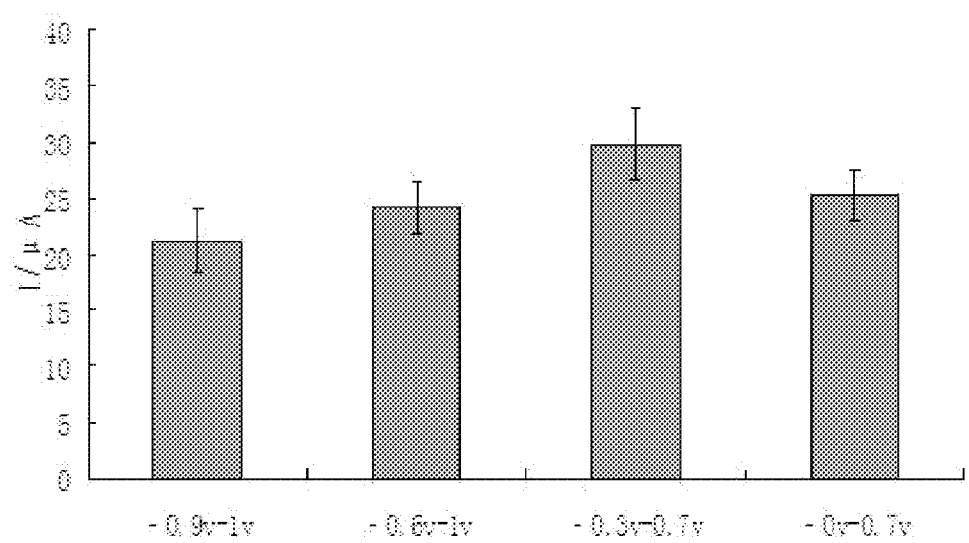
FIG. 6 shows the effect of cyclic voltammetric scanning potential on the current response of EPO and rhEPO electrochemical biosensor.

The invention involves optimization of major parameters that influence the current response of EPO and rhEPO electrochemical biosensor. The results show that the sensor's peak current is high with pH of the test base solution within 6.2~9.0, and is the highest with pH being 7.4. Therefore, the preferred pH of the test base solution ranges 6.2~9.0 and the most preferred pH is 7.4 (FIG. 4). While the incubation time of EPOR modified electrode and 500 ng/L EPO or rhEPO standard preparation solution increases from 5 minutes to 20 minutes, the sensor's peak current decreases gradually to minimum, and while the incubation time increases to 40 minutes, the peak current remains unchanged. It is suggested that after 20-minute incubation, EPO or rhEPO binding to EPOR modified electrode saturates. Therefore, the preferred incubation time of EPOR modified electrode and sample solution is 20 minutes or more, and the most preferred incubation time is 20 minutes (FIG. 5). In addition, the change in scanning potential affects $K_3[Fe(CN)_6]$—$K_4[Fe(CN)_6]$ redox peak potential insignificantly, but affects the sensor's current response markedly, particularly within −0.3 V~0.7 V (FIG. 6). The potential scanning speed affects the shape of cyclic voltammogram. The invention discovers that the allowed potential scanning speed ranges 10 mv/s~100 mv/s, but the cyclic voltammogram is the smoothest at 50 mv/s.

III. Electrochemical Biosensor Performance for EPO and rhEPO Detection

1. Specificity

EPOR modified electrode and the sample solution are co-incubated for 20 minutes, and electrochemical biosensor comprising EPOR modified electrode as working electrode, saturated calomel electrode as reference electrode, platinum electrode as counter electrode fabrication, and PBS solution containing 2 mmol/L $K_3[Fe(CN)_6]$—$K_4[Fe(CN)_6]$ (pH 7.4, 0.05 mol/L) as the test base solution is used for cyclic voltammetric scanning at room temperature, within the potential scanning range of −0.3V~0.7V, and with the potential scanning speed of 50 mv/s.

Figure 7:
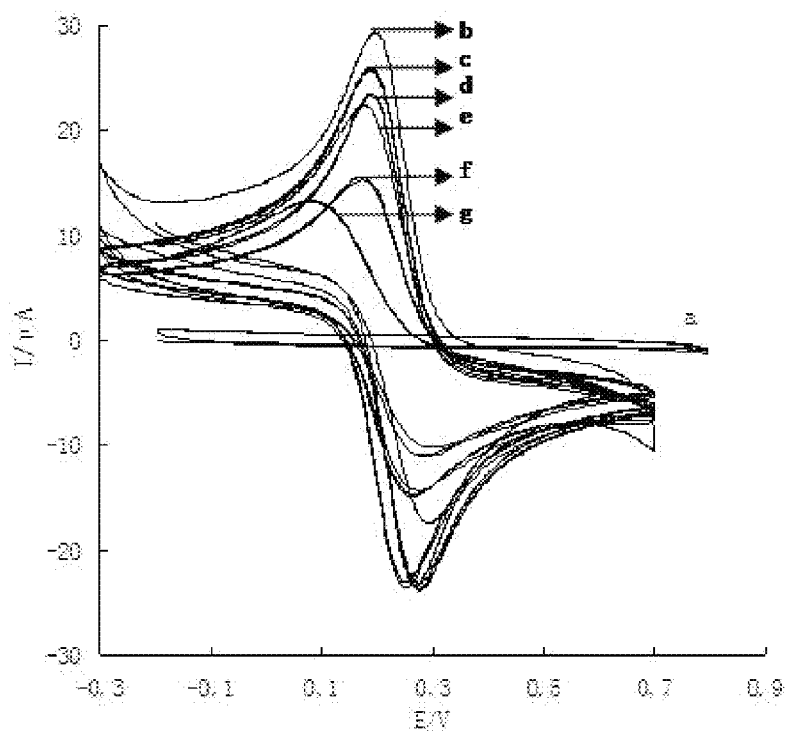
FIG. 7 shows the results of electrochemical response and specificity of electrochemical biosensor using EPOR modified electrode as working electrode. a: cyclic voltammogram of simple ZnO sol-gel modified electrode in PBS solution; b: cyclic voltammogram of unmodified glassy carbon electrode in PBS solution containing 2 mmol/L $K_3[Fe(CN)_6]$—$K_4[Fe(CN)_6]$; c: cyclic voltammogram of simple ZnO sol-gel modified electrode in PBS solution containing 2 mmol/L $K_3[Fe(CN)_6]$—$K_4[Fe(CN)_6]$; d: cyclic voltammogram of EPOR modified electrode in PBS solution containing 2 mmol/L $K_3[Fe(CN)_6]$—$K_4[Fe(CN)_6]$; e: cyclic voltammogram of EPOR modified electrode after 20-minute incubation in interfering substance containing solution (500 ng/L IgA, 500 ng/L IgG and 500 ng/L IgM); f: cyclic voltammogram of EPOR modified electrode after 20-minute incubation in solution containing 500 ng/L EPO standard preparation; g: cyclic voltammogram of EPOR modified electrode after 20-minute incubation in solution containing 500 ng/L rhEPO standard preparation.

The experimental results of the sensor's specificity are shown in FIG. 7. Curve a is the cyclic voltammogram for simple ZnO sol-gel modified electrode in PBS solution, which shows background current only; curve b is the cyclic voltammogram of unmodified glassy carbon electrode in PBS solution containing 2 mmol/L $K_3[Fe(CN)_6]$—$K_4[Fe(CN)_6]$. Because PBS solution is added with the redox probe $K_3[Fe(CN)_6]$—$K_4[Fe(CN)_6]$, the cyclic voltammogram changes markedly, which shows a pair of quasi-reversible redox peaks; curve c is the cyclic voltammogram of simple ZnO sol-gel modified electrode in PBS solution containing 2 mmol/L $K_3[Fe(CN)_6]$—$K_4[Fe(CN)_6]$. Because the ZnO sol-gel film deters electron transfer of electric conductive ions of the solution on the electrode, the redox peak currents decreased. Curve d representing the cyclic voltammogram of the EPOR modified electrode in 2 mmol/L $K_3[Fe(CN)_6]$/$K_4[Fe(CN)_6]$ PBS solution differs from curve c significantly, suggesting that EPOR modifies electrode surface successfully. As a biologic macromolecule, EPOR deters electron transfer once it has been absorbed onto the electrode surface, resulting in further decrease in the redox peak current when compared to curve c. Curve e representing the cyclic voltammogram of EPOR modified electrode after 20-minute incubation in interfering substance-containing solution (500 ng/L IgA, 500 ng/L IgG and 500 ng/L IgM) and curve d remain largely the same, suggesting that interfering substances, e.g., IgA, IgG, IgM do not affect EPO and rhEPO detection. curve f is the cyclic voltammogram of EPOR modified electrode after 20-minute incubation in 500 ng/L EPO standard preparation solution, and the response current changes by 8.2 µA before and after incubation (ΔI), and the peak current appears at the potential of 0.16V. EPO-EPOR complexes resulting from specific binding of EPO in the solution to EPOR on the electrode surface cover more electrode surface area, further deterring electron transfer. As a result, the redox peak current decreases markedly when compared to curve d. Curve g is the cyclic voltammogram of EPOR modified electrode after 20-minute incubation in 500 ng/L rhEPO standard preparation solution. The response currents change by 9.7 µA (ΔI) before and after incubation. Similarly, because rhEPO-EPOR complexes resulting from specific binding of rhEPO and EPOR deter electron transfer, the redox peak current decreases markedly when compared to curve d. Nevertheless, because rhEPO and EPO have different isoelectric points, rhEPO-EPOR complexes and EPO-EPOR complexes exhibit different working potentials. Compared to curve f, the redox peak shifts towards the negative potential in curve g, in which the peak current appears at the potential of 0.08V. EPO and rhEPO can be discriminated accurately according to the redox peak potential. These experimental results demonstrate that the invented EPOR modified electrode shows strong resistance to interference and high selectivity of EPO and rhEPO, and that it allows accurate discriminative detection of EPO and rhEPO.

2. Linear Range and Limit of Detection

Figure 8:
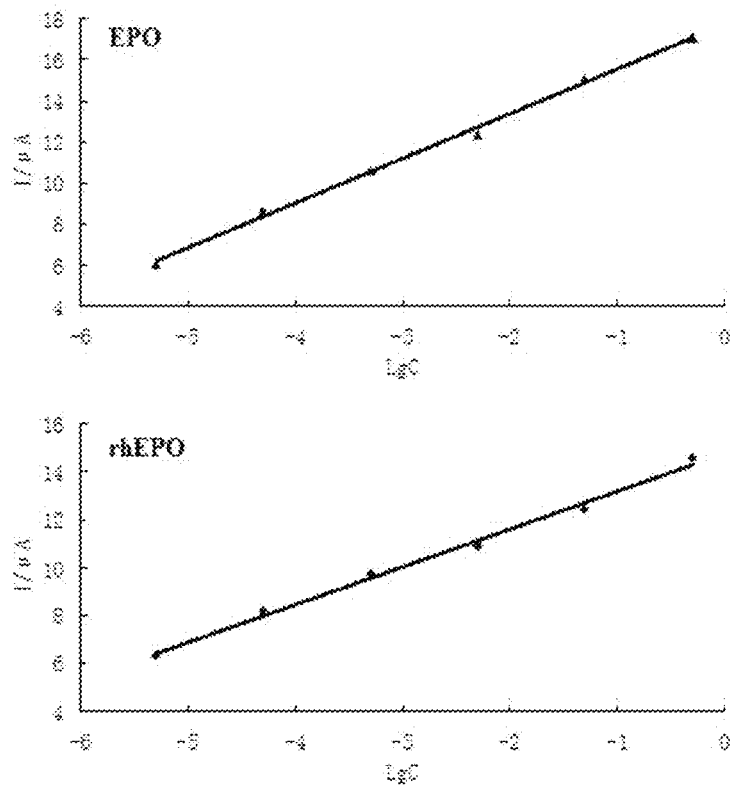
FIG. 8 shows EPO and rhEPO standard curves obtained using EPO and rhEPO electrochemical biosensor under optimal conditions.

EPOR modified electrode and the sample solution are co-incubated for 20 minutes, and EPO and rhEPO electrochemical biosensor comprising EPOR modified electrode as working electrode, saturated calomel electrode as reference electrode, platinum electrode as counter electrode fabrication, and PBS solution containing 2 mmol/L $K_3[Fe(CN)_6]$—$K_4[Fe(CN)_6]$ (pH 7.4, 0.05 mol/L) as the test base solution is used for cyclic voltammetric scanning at room temperature, within the potential scanning range of −0.3V~0.7V, and with the potential scanning speed of 50 mv/s. The results are shown in FIG. 8. When the EPO concentration ranges between 5 pg/L and 500 ng/L, the EPO concentration logarithmic value and the peak current exhibited a good linear relationship. For EPO, the linear regression equation was: y=2.1674x+17.691, the correlation coefficient is 0.9966 and the limit of detection is 0.5 pg/L. When the rhEPO concentration ranges between 5 pg/L and 500 ng/L, the rhEPO concentration logarithmic value and the peak current exhibited a good linear relationship. For rhEPO, the linear regression equation was: y=y=1.5737x+14.765, the correlation coefficient is 0.9935 and the limit of detection is 0.5 pg/L. These results show that the invented EPO and rhEPO electrochemical biosensor exhibits a wide linear range and a low limit of detection.

3. Stability

Figure 9:
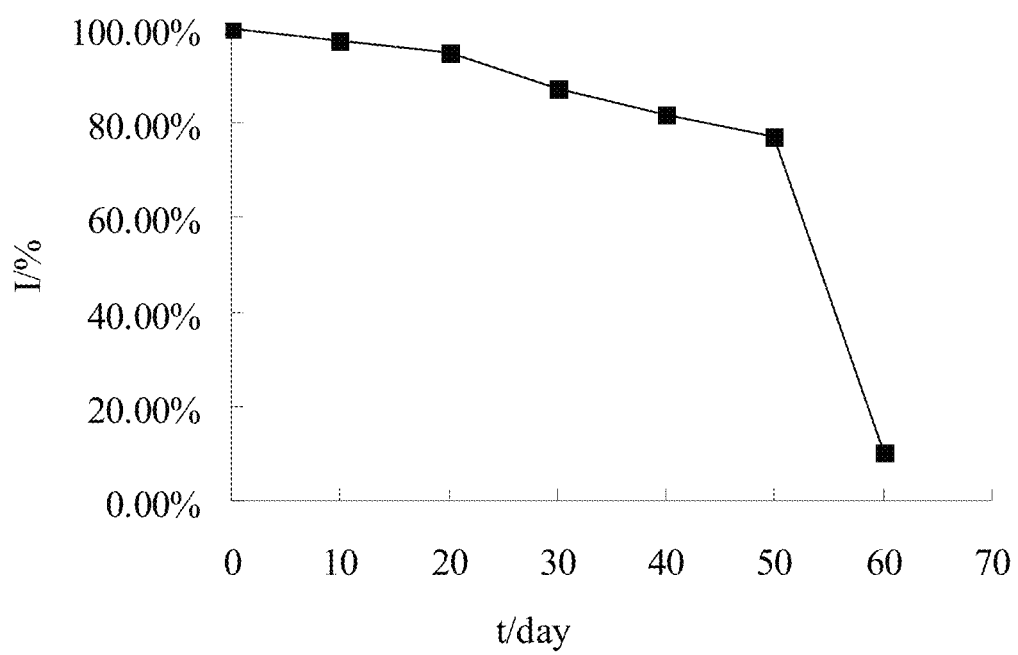
FIG. 9 shows current response changes of EPO and rhEPO electrochemical biosensor after various time periods of storage.

After storage of the newly prepared EPOR modified electrode at 4° C. in dark for 10, 20, 30, 40, 50, 60 days, electrochemical biosensor comprising the modified electrode, platinum electrode, and saturated reference electrode is used for cyclic voltammetric scanning in the test base solution containing 2 mmol/L $K_3[Fe(CN)_6]$—$K_4[Fe(CN)_6]$ PBS solution (pH 7.4, 0.05 mol/L) at room temperature with the potential scanning ranging −0.3V~0.7V and at the potential scanning speed of 50 mv/s, to investigate the stability of EPOR modified electrode. The results are shown in FIG. 9. After 20-day storage, the response current of EPOR modified electrode is approximately 95% of the original value; after 40-day storage, the response current is approximately 82% of the original value; after 50-day storage, the response current is approximately 77% of the original value. These results demonstrate that the invented EPOR modified electrode has good stability and long service life.

The above embodiments are intended to explain the technical protocol of the invention, and are not limited. Although the invention has been described through the invention's preferred embodiments, ordinary technical personnel working in this field should understand that various alterations in terms of form and detail may be implemented, without deviating from the invention's essence and range circumscribed by the enclosed claim form.

We claim:

1. An erythropoietin receptor modified electrode, comprising a glassy carbon electrode that is fixed with an erythropoietin receptor as a recognition element on a surface of the electrode via a ZnO sol-gel.

2. A method for preparing an erythropoietin receptor modified electrode in accordance with claim 1, comprising:
    (1) a carbon electrode pretreatment step that comprises burnishing, cleaning and drying a glassy carbon electrode surface so as to obtain a pretreated electrode;
    (2) a ZnO sol-gel preparation step that comprises dissolving zinc acetate in absolute alcohol to obtain a zinc acetate mixture and adding lithium hydroxide to the zinc acetate mixture while subjecting the zinc acetate mixture to ultrasound stirring to obtain a ZnO sol-gel solution; and
    (3) an erythropoietin receptor fixation step that comprises mixing an erythropoietin receptor solution with the ZnO sol-gel solution so as to obtain a fixation solution, dripping the fixation solution on the glassy carbon electrode surface of the pretreated electrode obtained in (1) so as to obtain a treated electrode, followed by drying and washing the treated electrode to obtain the erythropoietin receptor modified electrode.

3. The method of claim 2, wherein in (1), burnishing the glassy carbon electrode surface comprises burnishing with a first aluminum oxide powder having a particle size of 0.3 μm, washing the electrode with water followed by sequentially washing the electrode in an ultrasound bath comprising nitric acid, acetone and water, respectively, and then burnishing with a second aluminum oxide power having a particle size of 0.05 μm.

4. The method of claim 2, wherein in (2), the zinc acetate mixture has a concentration of 0.1 mol/L, the ZnO sol-gel solution has a concentration of 0.067 mol/L, and before the ZnO sol-gel solution is mixed with the erythropoietin receptor solution in (3), the ZnO sol-gel solution is diluted with absolute alcohol at a vol/vol ratio of between 2:1 to 1:3.

5. The method of claim 4, wherein the ZnO sol-gel solution is diluted with absolute alcohol at a vol/vol ratio of 1:2.

6. The method of claim 2, wherein in (3), the ZnO sol-gel solution is mixed with 10 ng to 100 μg/L of the erythropoietin receptor solution with a vol/vol ratio of between 4:1 to 1:1.15, and wherein drying the treated electrode comprises air drying the treated electrode, and washing the treated electrode comprises washing the treated electrode in phosphate buffer.

7. The method of claim 6, wherein in (3), the ZnO sol-gel solution is mixed with 1 μg/L of the erythropoietin receptor solution with a vol/vol ratio of 1:1.

8. An electrochemical biosensor for erythropoietin and recombinant human erythropoietin, comprising:
    a working electrode that is the erythropoietin receptor modified electrode of claim 1;
    a counter electrode that is a platinum electrode;
    a reference electrode that is a saturated calomel electrode; and
    a test base solution is a phosphate buffer having a pH of between 6.2~9.0 and comprises 2 mmol/L of $K_3[Fe(CN)_6]$ and 2 mmol/L of $K_4[Fe(CN)_6]$.

9. The electrochemical biosensor of claim 8, wherein the phosphate buffer has a pH of 7.4.

10. A method of detecting erythropoietin and/or recombinant human erythropoietin using the electrochemical biosensor of claim 8, comprising: co-incubating the erythropoietin receptor modified electrode with a sample solution, performing a cyclic voltammetric scanning using the electrochemical biosensor with a potential scanning range of −0.3V to 0.7V and with a potential scanning speed of 10 mv/s to 100 mv/s, wherein a concentration of an erythropoietin within the sample solution is calculated according to a peak current at a potential of 0.14V to 0.17V and an erythropoietin standard curve and/or wherein a concentration of a recombinant human erythropoietin is calculated according to a peak current at a potential of 0.06V to 0.09V and a recombinant human erythropoietin standard curve.

* * * * *